United States Patent [19]
Liprie

[11] Patent Number: 5,322,499
[45] Date of Patent: Jun. 21, 1994

[54] CONTINUOUS SHEATED LOW DOSE RADIACTIVE CORE ADAPTED FOR CUTTING INTO SHORT SEALED SEGMENTS

[76] Inventor: Sam F. Liprie, 424 W. McNeese St., Lake Charles, La. 70605

[21] Appl. No.: 899,348

[22] Filed: Jun. 16, 1992

Related U.S. Application Data

[63] Continuation-in-part of Ser. No. 61,468, Jun. 15, 1987, abandoned, which is a continuation-in-part of Ser. No. 897,544, Aug. 18, 1986, abandoned, which is a continuation-in-part of Ser. No. 778,410, Sep. 20, 1985, abandoned.

[51] Int. Cl.$^5$ ............................................. A61N 5/10
[52] U.S. Cl. .................................... 600/8; 600/3
[58] Field of Search ......................... 600/1, 3, 6–8; 250/496.1, 507.1

[56] References Cited

U.S. PATENT DOCUMENTS

| | | | |
|---|---|---|---|
| 4,697,575 | 10/1987 | Horowitz | 600/8 |
| 4,702,228 | 10/1987 | Russell, Jr. et al. | 600/8 |
| 4,946,435 | 8/1990 | Suthanthiran et al. | 600/1 X |
| 4,994,013 | 2/1991 | Suthanthiran et al. | 600/8 |

Primary Examiner—Francis Jaworski
Attorney, Agent, or Firm—O'Connor, Cavanagh

[57] ABSTRACT

A method of forming implantable low dose solid radioactive segments of desired lengths sealed against end leakage of radioactive particles, for use in brachytherapy of malignant tumors. The segments are separated from a single continuous elongate assembly of composite material which includes a continuous solid radioactive elongate core at least partly composed of iridium, sufficiently brittle to break cleanly when cut transverse to its longitudinal axis, encased along substantially its entire longitudinal surface in a sheath having a predetermined thickness and composed of substantially pure platinum or other metal which is malleable relative to the hardness of the core and, when irradiated, has a half-life much shorter than that of the core. When a radioactive segment of selected length is needed for use as a brachytherapy implant, the continuous assembly is cut transversely to provide the selected length, using a pair of scissors having opposed blunt blades, by bringing a portion of the assembly transversely between the blunt blades and thereupon exerting a cutting force on the assembly lying therebetween to break the core cleanly at that point while squeezing the sheath firmly about the newly cut end of the core to encapsulate and substantially seal it within the sheath against radioactive leakage at the newly cut end.

5 Claims, 2 Drawing Sheets

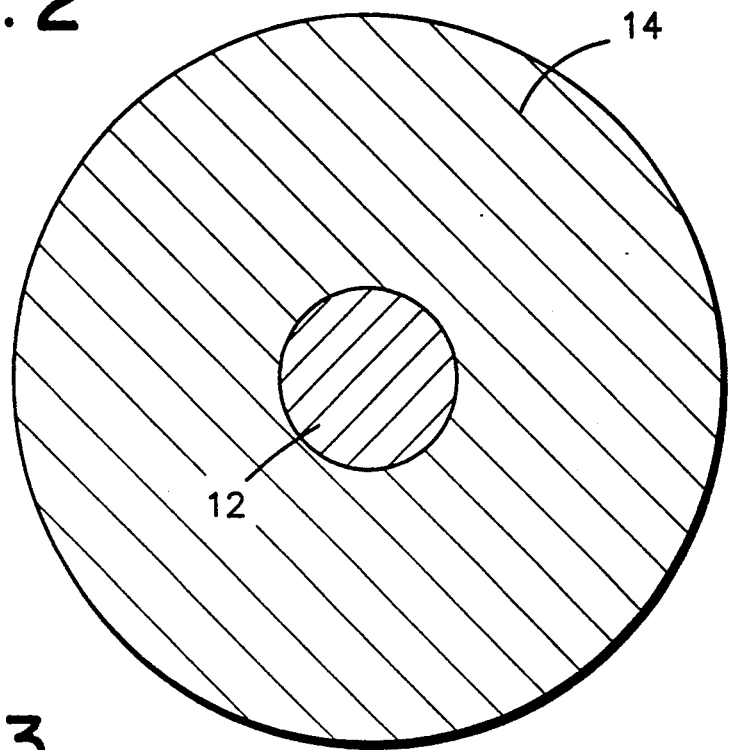
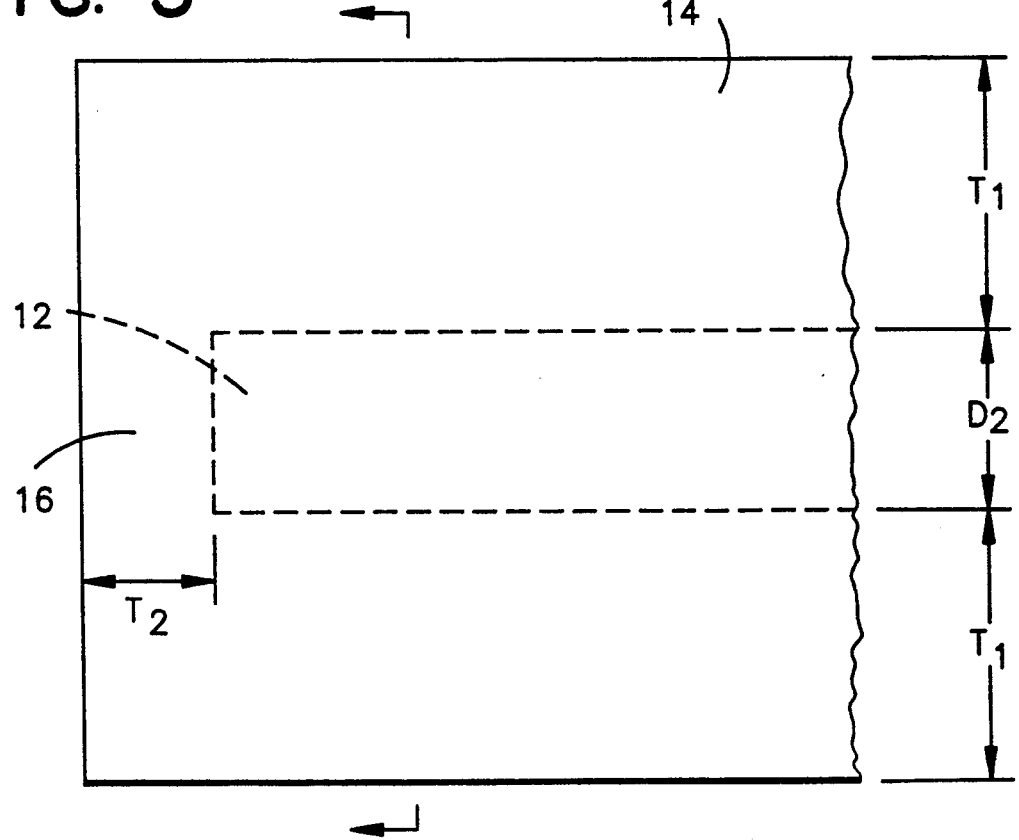

CONTINUOUS SHEATED LOW DOSE RADIACTIVE CORE ADAPTED FOR CUTTING INTO SHORT SEALED SEGMENTS

CROSS-REFERENCE TO RELATED APPLICATIONS

This application is a continuation-in-part of copending application Ser. No. 07/061,468 filed Jun. 15, 1987, and now abandoned which is a continuation-in-part of Ser. No. 06/897,544 filed Aug. 18, 1986, which is a continuation-in-part of Ser. No. 06/778,410 filed Sep. 20, 1985, the latter two of which have also been abandoned.

BACKGROUND OF THE INVENTION

1. Field of the Invention

The present invention relates generally to implantable elements for treatment of malignant tumors in the body, and more particularly, to a radioactive filament or core comprised at least partly of substantially pure iridium, and preferably an iridium/platinum alloy, encompassed within a substantially pure platinum sheath, which is adapted to be cut into predetermined sealed lengths without undesirable leakage of radioactivity at the ends of each cut length, for insertion into and shrinkage of body tumors.

2. General Background

In the field of medicine which addresses the treatment of tumors in the body, one such method of treatment, referred to as interstitial brachytherapy, involves insertion into the tumor of implants which have been irradiated to enable them to emit radioactivity, for the purpose of shrinking and ultimately destroying the tumor.

The procedure followed for this type of therapy calls for inserting the radioactive implant through a plastic catheter or similar means previously inserted into the tumor from a point external to the body. The intention is that when the implant is within the tumor, the radioactivity emitted by the implant is sufficient to destroy the cancerous cells in the immediate vicinity. Unfortunately, however, problems exist in using implants of the type presently available on the market. A very common type is the IR-192 isotope in the form of iridium/platinum seeds spaced within a nylon or plastic tube for insertion into the cancerous growth. Typically, the IR-192 seeds are three millimeters (mm) in length and spaced seven mm apart in a configuration which provides a known standard distance of one centimeter (cm) between the centers of adjacent seeds. The IR-192 isotope of the seeds should not be exposed at the exterior surfaces because radioactivity bleeding therefrom could cause serious injury to the adjacent tissue. It is essential, therefore, that the iridium/platinum core be housed in a sheath of platinum at all times. The spacing between seeds in the nylon or plastic tubing which is inserted in the body tumor results in only partial treatment of the tumor because of the lack of uniform emission of radioactivity from the tubing.

Similarly, there are instances in which the tubing containing the IR-192 seeds must be inserted along a path of the body which is not straight, such as would be the case in use of an endobronchial implant, tongue implant, tonsil implant or other implant intended to reach a region of the body not readily accessible for purposes of the treatment. In these instances, it is essential to install a catheter through which the implant tube may be guided as it is inserted to the site of the tumor within the body. The catheter produces a tortuous path or must be installed along such a path, consisting of many turns, tight angles and curves to provide a passage to the location within the body requiring treatment. The IR-192 implant typically must be threaded through such a path, and, because of spacing of the seeds within the tubing of the implant, the traversal of the implant may produce bending or kinking of the catheter or of the tubing of the implant itself, to effectively prevent further movement of the implant and thereby, preclude it from reaching the desired treatment site.

Another prior art type of radioactive implant is marketed in the form of encapsulated IR-192 wires of predetermined length. This implant type is advantageous compared to the seed type described above, because it provides a continuous surface for relatively uniform emission in contrast to the gaps encountered between radioactive portions of the seed type. However, the continuous surface type suffers the limitation that it must be marketed in prefabricated pieces of pre-cut lengths which may be too short or too long for the tumor under treatment. The prefabricated implant cannot readily be trimmed or cut to a desired length at the time it is to be introduced into the patient's body because the cut ends will leak, and damage the surrounding tissue.

Current guidelines for use of radioactive sealed sources such as these implants, require that the source be leak tested at least every six months. The known types of implants meet this guideline since they are carefully sealed at the point of manufacture by complete encapsulation. As noted above, this is not conducive to on-site flexibility of treatment of the various sizes of body tumors requiring treatment. It would be desirable to provide a low dose radioactive implant which is adapted to be trimmed to proper desired length at the point of treatment, rather than fabricated in many different lengths at the point of manufacture and thereby necessitating large inventories of such implants at the treatment facility.

Exemplary of the pertinent prior art are the following U.S. Pat. No. 2,429,438 in the name of Wappler pertaining to tubular bodies such as radium seeds; U.S. Pat. No. 2,322,902, also in the name of Wappler, on apparatus for making such tubular bodies; and U.S. Pat. No. 3,438,365 to Packer et al. on radioactive seed containing xenon gas for medical treatment.

SUMMARY OF THE INVENTION

The present invention provides a composite implant which is of the solid wire type but which is adapted to overcome the deficiencies of the prior art implants in a simple and effective manner. In a presently preferred embodiment, an IR-192 composite implant has a solid wire core composed at least partly of iridium, such as 25% iridium and 75% platinum, of approximately 0.1 mm diameter. The core area is encased in a 100% platinum or substantially pure platinum sheath having a thickness of about 0.15 mm in planes (cross-sections) normal to its longitudinal axis and a thickness of about 0.075 mm at its end portions. Accordingly, the diameter of such an implant is only 0.4 mm.

According to an important feature of the invention, composite implant material is fabricated in a continuous length which is longer than that of the implant dimension required for treatment of a tumor or tumors of anticipated size, and is configured to allow cutting or trimming of the material to desired shorter implant length(s) at the place and time that the implant procedure is to be performed. The cutting is performed substantially perpendicularly to the axis of the fiber core, in a manner which assures that the sheath layer is squeezed about the new end portion of the core as the composite material is being cut, to simultaneously produce a thinner but effective layer, e.g., 0.075 mm, at the cut end, so that, despite having been cut, the core end is now actually encased in the sheath. In this manner, the ends of each final trimmed implant are sealed against undesirable leakage and potential unshielded contact with tissue, and the implant itself can be cut to virtually any desired length from a spool or roll of the composite material thereby avoiding the need to maintain a large inventory of pre-cut implants of different lengths.

The invention also provides various methods for fabricating and ultimately segmenting the composite material, and for treating tumors with the implantable segments of selected length(s) separated from the composite material, including separation of each implantable segment while maintaining the end portions thereof sealed by the sheath upon completion of the separation or segmentation step.

Therefore, it is a principal object of the present invention to provide a spool of continuous elongate composite solid wire/sheath implant material for use in low dosage brachytherapy, wherein the material is adapted or configured to be cut to desired length(s) suitable for treatment of malignant tumors at the time and place of performing the treatment.

It is another important object of the present invention to provide an elongate composite solid sheathed radioactive core which may be cut as and when desired by the physician or technician to suitable fully sheathed length(s) for treatment of deep body tumor(s) of virtually any anticipated size which may be treated by low dosage brachytherapy.

Still another object of the present invention is to provide a method for fabricating elongate low dosage radioactive core material encapsulated in a sheath and suitable to be trimmed to size as and when needed for in-body treatment of cancerous growths.

Yet another object of the invention is to provide a method for separating uniform elongate low dosage radioactive core material encapsulated in a sheath into individual smaller lengths of desired size for implantation to treat malignant tumors, wherein the separation method produces individual lengths of the material with sealed ends to prevent leakage of radioactive particles therefrom.

A further object of the invention is to provide a method for treating malignant tumors by brachytherapy using one or more low dose radioactive source wires sized to be implanted at the tumor site(s), in which the source wires are appropriately sized from a continuous length of material as needed at the time of treatment.

Another object of the invention is to provide an elongate iridium/platinum roll from which implants for low dosage radioactive treatment of tumors may be cut to desired length(s) and each end simultaneously sealed against leakage of radioactivity as it is being cut.

BRIEF DESCRIPTION OF THE DRAWINGS

The above and still further objects, aspects, features and attendant advantages of the present invention will become apparent from a consideration of the following detailed description of a preferred embodiment and method thereof, taken in conjunction with the accompanying drawings, in which:

FIG. 2 is a cross-sectional view of the composite material of FIG. 1;

FIG. 3 is a partial side view at or near an end of the composite material of FIG. 1;

DETAILED DESCRIPTION OF THE PREFERRED EMBODIMENT AND METHODS

Figure 1:
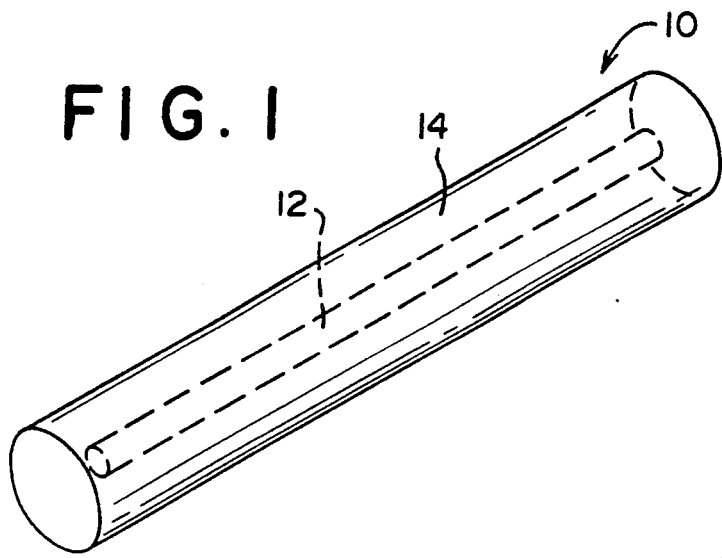
FIG. 1 is a perspective view of a continuous length of composite implant material intended to be separated into desired smaller lengths at a subsequent time according to the invention.

Referring now to the drawings, which are not intended to be to scale, a continuous length 10 of composite material for separation into brachytherapy implants of shorter length(s) is illustrated in FIG. 1. The material is in the configuration of a solid elongate core member 12 of wire or fiber preferably composed at least partly of iridium or other material capable of being irradiated to a desired level of radioactivity for low dosage brachytherapy, encapsulated in a sheath 14 (see, also, FIG. 2). Although an exemplary length 10 of the composite material is shown in FIG. 1, it will be readily understood from the ensuing description herein that the material may be supplied in considerably longer lengths, spools or rolls, to be maintained in inventory at a treatment center (e.g., a hospital or other institution) for separation into implantable segments of desired lengths as needed for treating malignant tumors of specific sizes. The original continuous length 10 of composite material having the characteristics and properties described herein, in spooled or other form, may be manufactured by any known method, the important consideration being the availability of such a continuous length at the treatment center for segmentation as needed.

In a presently preferred embodiment, the extended length 10 of composite material has an iridium/platinum alloy core 12 such as of at least 25% substantially pure iridium and the remainder (75% or less, according to the percentage of the iridium component) of substantially pure platinum, for example, although other suitable alloy or single element radioactive core material may be used instead. The sheath 14 is preferably composed of substantially pure platinum, although, here also, a suitable alternative material may be used, an important property of the sheath being that, when irradiated, it should have a half-life much shorter than that of the core. The sheath is intended to seal the radioactive core against direct or substantially unshielded contact with surrounding tissue when the composite element is implanted for treatment. Such contact may result in severe damage to surrounding or adjacent healthy tissue, including tissue encountered during insertion and/or withdrawal of the implant as well as tissue in the vicinity of the tumor site. Sheath 14 is intended, further, to filter out Beta radiation emanating from the radioactive core 12 while allowing passage of Gamma radiation from the core to irradiate and produce shrinkage (and ultimately, destruction) of the tumor under treatment.

Exemplary dimensions of the continuous length 10 of composite material having such composition are (i) a length which, of course, is limited only by the practicalities of manufacture, handling and storage, (ii) a core 12 diameter of approximately 0.1 mm ($D_1$, FIG. 3), (iii) a sheath 14 thickness along the longitudinal surface of the core of approximately 0.15 mm ($T_1$, FIG. 3), and (iv) a sheath 14 thickness at each end surface of the composite material of approximately 0.075 mm ($T_2$, FIG. 3).

It is to be stressed that although the actual dimensions will depend upon the specific materials employed within the composite material, it is crucial that the dimensions be set according to the brittleness, hardness (softness) and malleability of the core and the sheath for reasons which will become apparent in the description of the process of segmentation of the continuous length into implantable radioactive segments of desired length, below. Of particular importance is the feature that the freshly cut end of each implantable segment (and of the remaining composite material on the spool or roll) formed by separation of a desired shorter length from the continuous length 10 of composite material should comprise an end of the solid core 12 which is substantially sealed within a layer of the sheath 14.

Indeed, it is highly desirable to have the capability to simply manufacture a continuous length of such composite material with solid radioactive core which may be supplied in a spool, roll or other configuration of relatively substantial length to a treatment center, without any factory precutting or presetting of segment lengths thereon, for subsequent segmentation into desired length(s) at the time of treatment on an as-needed basis. Heretofore, this capability alone has not existed owing to the excessive leakage of radioactive particles (contamination) which would have resulted at the severed ends of the implant, before the advent of the present invention.

Figure 4:
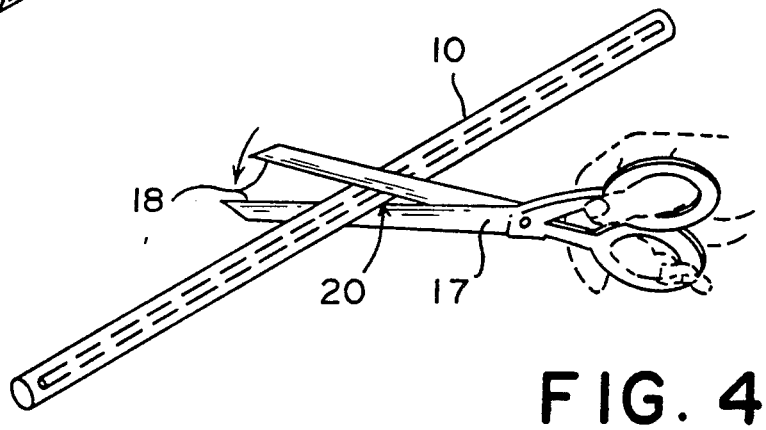
FIG. 4 is a perspective view of a continuous length of the composite material of FIG. 1 in the process of being cut or trimmed to a desired smaller length required for a specific implant according to the invention.
Figure 5:
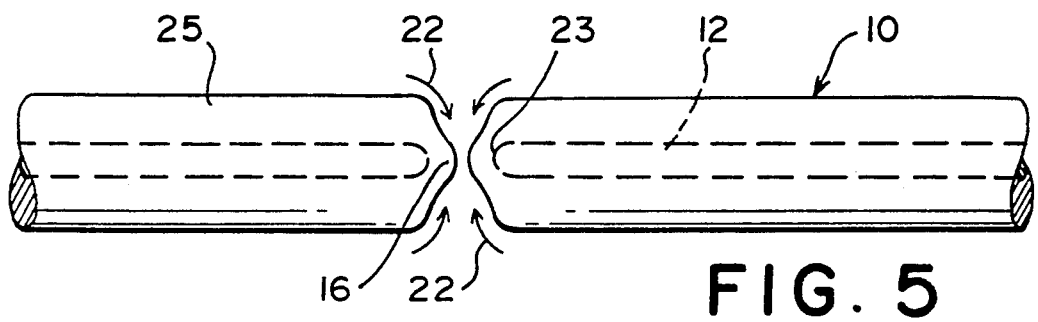
FIG. 5 is a partial side view of the cut end of an implant of desired length and of the resulting end of the composite material of FIG. 1 from which the smaller length of implant was cut.

Referring now to FIGS. 4 and 5, the continuous length 10 of composite material is separated into implantable segments 25 of shorter length when, as and if needed for brachytherapy treatment, according to the following method. In the process of segmentation at the treatment center, the continuous length 10 of the composite material is cut at a point 20 measured from a free end of the material to provide the desired length of implantable segment(s) for use in treating the tumor, according to the measured size of the tumor (detected by any known means) or its estimated size. It is noteworthy that the continuous length would not be marked with preset individual length indicia or itself fabricated in a way that precludes cuts from being made at other than predetermined, pre-measured points along its length. To do so, in any way that confines the separations to preset points, rather than at arbitrarily selected points which depend solely on particular size of the tumor to be treated, would defeat the important aspect of flexibility of on-site selection of the length of the very next segment to be removed from the spool. Rather, the continuous length of composite material as taught by the present invention is relatively uniform throughout, including its overall diameter (i.e., no depressions at particular points along its length), so that each separated segment will likewise be substantially uniform.

According to another important aspect of the method of severing the continuous length 10 into shorter lengths of individual implantable segments 25 according to the invention, a scissors 17 (or other suitable cutting instrument) is used which is intentionally provided with dulled blades 18 (or dulled other cutting edges, as the case may be). The purpose is to allow the cut to be made at point 20 by a technique of pinching off the segment 25 from the length 10, as the blunt scissors are being closed (or such other cutting edges drawn together) over the length of composite material at the selected point in a direction substantially normal to the longitudinal axis of the continuous length 10. In doing so, the wall of sheath 14 is simultaneously squeezed over the solid core 12 in the directions indicated by arrows 22 (FIG. 5).

With a core sufficiently brittle to break cleanly under the forces exerted by the dulled blades, and a sheath sufficiently malleable relative to the hardness of the core to be squeezed and stretched to a thinner wall thickness and ultimately over the respective ends 23 of the now separated core on continuous length 10 and segment 25 as the blades are finally closed, the freshly cut ends are sealed by sheath portions 16 against leakage of radioactive particles from the core into the external environment. These characteristics and properties of the core and the sheath are present in the material compositions dimensioned as indicated for the presently preferred embodiment described in conjunction with FIGS. 1–3. Despite the desired degree of brittleness of the core 12, it is not so brittle that it would break if the continuous length 10 of composite material were wound on a spool, provided that the hub of the spool is greater than a diameter which is readily determined by experimentation.

The severed implantable radioactive segments produced by the method of the invention are also well adapted to traverse a tortuous path within the body to the site of the tumor under treatment, such as through a catheter consisting of many turns, tight angles and curves, without the type of binding often encountered with seed-type implants.

Figure 6:
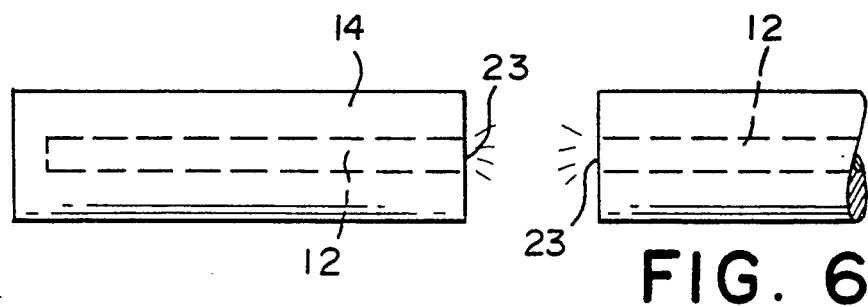
FIG. 6 is a partial side view of the end of an improperly separated length intended for implant and of the companion end of composite material from which the smaller length of implant was separated.

Referring now to FIG. 6, an improper cutting of the segment from the continuous length of composite material, such as by use of scissors having blades which are too sharp or of implant materials having undesirable characteristics and properties (including inappropriate dimensions) in this regard, would result in exposure of the radioactive core at each of the cut ends. The clean cut of the sheath and extending end portion 23 of the core 12 is intentionally exaggerated to highlight this set of events. In situations where the cut produces substantial sealing of the cut end of the core by the squeezed sheath, but leaves some small degree of exposure, the freshly cut end of the severed segment may be dipped into a small quantity of the quick-drying adhesive cement marketed under the name Super Glue (cyanoacrylate ester) or the like which, when allowed to harden, assists in forming a complete seal at the end portion.

Although a presently preferred embodiment and preferred methods having been described herein according to the invention, it will be appreciated by persons skilled in the relevant art that variations and modifications of the disclosed implementation and methods may be made without departing from the spirit and scope of the invention. Accordingly, it is intended that the invention shall be limited only to the extent required by the appended claims and the principles and rules of applicable law.

What is claimed is:

1. A method of forming radioactive implants into desired lengths, while sealing end portions of each length, the method comprising the following steps:
   a. providing a solid radioactive alloy core of at least 25% iridium and the remainder platinum;
   b. surrounding the alloy core with a pure metallic platinum sheath to at least a thickness of 0.15 millimeters;
   c. providing scissors for cutting the implant, said scissors having opposed blunt blades; and
   d. squeezing the implant between the blunt blades so that the alloy core is cut and the pure metallic sheath encasing the core is squeezed around the end of the core to at least 0.075 mm in thickness for sealing the alloy core of the cut length.

2. A method of forming low dose solid radioactive implants of desired lengths sealed against end leakage of radioactive particles, from a single continuous length of composite material, for use in brachytherapy of malignant tumors, comprising:

providing a continuous solid radioactive elongate core at least partly composed of iridium, sufficiently brittle to break cleanly when cut transverse to its longitudinal axis;

encasing substantially the entire longitudinal surface of the core in a sheath having a predetermined thickness and composed of a substantially pure metal such as platinum which is malleable relative to the hardness of the core and, when irradiated, has a half-life much shorter than that of the core, to form a continuous assembly: and cutting the continuous assembly transversely into segments of lengths desired for brachytherapy implants, using a pair of scissors having opposed blunt blades, by bringing a portion of the assembly transversely between the blunt blades and thereupon exerting a cutting force on the assembly lying therebetween to break the core cleanly thereat while squeezing the sheath firmly about the newly cut end of the core to encapsulate and substantially seal it within the sheath against radioactive leakage at the newly cut end, the sheath thickness being sufficient to preclude rupture thereof anywhere but in a direction substantially transverse to the longitudinal axis of the assembly at the point of exertion of the cutting force.

3. The method of claim 2, further including:

covering any exposed portion of the newly cut end of the core substantially sealed by the sheath with a coating material adapted to form a complete seal at that end of the segment.

4. The method of claim 3, wherein:

the coating material is cyanoacrylate ester.

5. A method of treating in-body tumors by low dosage brachytherapy, which comprises:

measuring or estimating the size of the tumor to be treated, retrieving a continuous length of composite solid radioactive material having a central radioactive core and a sheath surrounding the longitudinal surface of the core, said continuous length being considerably greater than the length of a brachytherapy implant required to treat the tumor, and severing an end segment of suitable length for treating the tumor from the continuous length of composite material while sealing the severed end of the segment, and using the severed segment as a brachytherapy implant to treat the tumor.

* * * * *